US005455060A

United States Patent [19]

Neamy et al.

[11] Patent Number: 5,455,060
[45] Date of Patent: Oct. 3, 1995

[54] COMPACTED FABRICS FOR ORTHOPEDIC CASTING TAPES

[75] Inventors: Scott A. Neamy, Hugo; James C. Novack, St. Paul; Matthew T. Scholz, Woodbury, all of Minn.

[73] Assignee: Minnesota Mining and Manufacturing Company, St. Paul, Minn.

[21] Appl. No.: 141,830

[22] Filed: Oct. 25, 1993

[51] Int. Cl.⁶ .......................... A61L 15/14; A61F 13/04; B05D 3/02

[52] U.S. Cl. ..................... 427/2.31; 427/314; 427/389.8; 427/227

[58] Field of Search .................. 427/2.31, 214, 427/314, 389.8, 227

[56] References Cited

U.S. PATENT DOCUMENTS

| | | | |
|---|---|---|---|
| 2,765,513 | 10/1956 | Walton | 26/18.6 |
| 3,077,655 | 2/1963 | Runton | 26/18.5 |
| 3,421,501 | 1/1969 | Beightol | 128/90 |
| 3,454,202 | 7/1969 | Kearn | 427/389.8 |
| 3,630,194 | 12/1971 | Boardman | 128/90 |
| 3,686,725 | 8/1972 | Nisbet et al. | 28/74 R |
| 3,787,272 | 1/1974 | Nisbet et al. | 161/89 |
| 3,793,686 | 2/1974 | Nisbet | 28/75 R |
| 3,837,338 | 9/1974 | Chesky et al. | 128/156 |
| 3,908,644 | 9/1975 | Neinart et al. | 128/90 |
| 3,932,526 | 1/1976 | Koshar | 260/607 A |
| 3,972,323 | 8/1976 | Boricheski | 128/91 R |
| 4,041,581 | 8/1977 | Diggle, Jr. | 26/18.6 |
| 4,131,114 | 12/1978 | Kirkpatrick et al. | 128/90 |
| 4,134,397 | 1/1979 | Gianakakos et al. | 128/90 |
| 4,376,438 | 3/1983 | Straube et al. | 128/90 |
| 4,411,262 | 10/1983 | von Bonin et al. | 128/90 |
| 4,433,680 | 2/1984 | Yoon | 128/90 |
| 4,441,262 | 4/1984 | Gazzoni | 34/57 D |
| 4,473,671 | 9/1984 | Green | 523/105 |
| 4,502,479 | 3/1985 | Garwood et al. | 128/90 |
| 4,609,578 | 9/1986 | Reed | 428/76 |
| 4,667,661 | 5/1987 | Scholz et al. | 128/90 |
| 4,668,563 | 5/1987 | Buese et al. | 428/230 |
| 4,672,956 | 6/1987 | Potter et al. | 427/2.31 |
| 4,704,113 | 11/1987 | Schoots | 604/379 |
| 4,705,840 | 11/1987 | Buckanin | 528/53 |
| 4,745,912 | 5/1988 | McMurray | 128/90 |
| 4,800,872 | 1/1989 | Buese et al. | 128/90 |
| 4,841,958 | 6/1989 | Ersfeld et al. | 128/90 |
| 4,940,047 | 7/1990 | Richter et al. | 128/90 |
| 4,947,839 | 8/1990 | Clark et al. | 128/90 |
| 4,984,566 | 1/1991 | Sekine et al. | 128/90 |
| 5,014,403 | 5/1991 | Buese | 28/170 |
| 5,027,804 | 7/1991 | Forsyth et al. | 128/90 |
| 5,060,349 | 10/1991 | Walton et al. | 26/18.6 |
| 5,088,484 | 2/1992 | Freeman et al. | 128/89 R |
| 5,169,698 | 12/1992 | Behjati et al. | 428/68 |
| 5,256,134 | 10/1993 | Ingham | 602/8 |
| 5,370,927 | 12/1994 | Scholz | 427/2.31 |

FOREIGN PATENT DOCUMENTS

0407056A2   1/1991   European Pat. Off. .

OTHER PUBLICATIONS

Derwent Abstract No. 48103 of German Patent 2933926, Mar. 1981.

*Primary Examiner*—Diana Dudash
*Attorney, Agent, or Firm*—Gary L. Griswold; Walter N. Kirn; F. Andrew Ubel

[57] ABSTRACT

The present invention provides an article, comprising: a fabric sheet which has been compacted using a heat shrink yarn; and a curable or hardenable resin coated onto the fabric sheet. The present invention involves compacting a fabric sheet to impart stretchability and conformability to the fabric while minimizing undesirable recovery forces. Suitable fabrics for compacting are fabrics which comprise fiberglass fibers which are capable of first being compacted and then being heat set or annealed in the compacted state. The article may be in the form of an orthopedic bandage and may optionally contain a microfiber filler associated with the resin.

19 Claims, 3 Drawing Sheets

COMPACTED FABRICS FOR ORTHOPEDIC CASTING TAPES

FIELD OF THE INVENTION

This invention relates to sheet materials coated with a curable or hardenable polymeric resin. More particularly, this invention relates to a curable or hardenable resin coated sheet material useful in preparing an orthopedic bandage.

BACKGROUND OF THE INVENTION

Many different orthopedic casting materials have been developed for use in the immobilization of broken or otherwise injured body limbs. Some of the first casting materials developed for this purpose involve the use of plaster of Paris bandages consisting of a mesh fabric (e.g., cotton gauze) with plaster incorporated into the openings and onto the surface of the mesh fabric.

Plaster of Paris casts, however, have a number of attendant disadvantages, including a low strength-to-weight ratio, resulting in a finished cast which is very heavy and bulky. Furthermore, plaster of Paris casts typically disintegrate in water, thus making it necessary to avoid bathing, showering, or other activities involving contact with water. In addition, plaster of Paris casts are not air permeable, thus do not allow for the circulation of air beneath the cast which greatly facilitates the evaporation and removal of moisture trapped between cast and skin. This often leads to skin maceration, irritation, or infection. Such disadvantages, as well as others, stimulated research in the orthopedic casting art for casting materials having improved properties over plaster of Paris.

A significant advancement in the art was achieved when polyisocyanate prepolymers were found to be useful in formulating a resin for orthopedic casting materials, as disclosed, for example, in U.S. Pat. No. 4,502,479 (Garwood et al.) and U.S. Pat. No. 4,441,262 (Von Bonin et al.). U.S. Pat. No. 4,502,479 sets forth an orthopedic casting material comprising a knit fabric which is made from a high modulus fiber (e.g., fiberglass) impregnated with a polyisocyanate prepolymer resin which will form a polyurea. Orthopedic casting materials made in accordance with U.S. Pat. No. 4,502,479 provide significant advancement over the plaster of Paris orthopedic casts, including a higher strength-to-weight ratio and greater air permeability. However, such orthopedic casting materials tend not to permit tactile manipulation or palpation of the fine bone structure beneath the cast to the extent possible when applying a plaster of Paris cast. In this regard, knit fiberglass materials are not as compressible as plaster, and tend to mask the fine structure of the bone as the cast is applied, e.g., the care provider may be limited in "feeling" the bone during reduction of the fracture.

Fiberglass backings have further disadvantages. For example, fiberglass backings are comprised of fibers which have essentially no elongation. Because the fiber elongation is essentially nil, glass fabrics do not stretch unless they are constructed with very loose loops which can deform upon application of tension, thereby providing stretching of the fabric. Knitting with loosely formed chain stitches imparts extensibility by virtue of its system of interlocking knots and loose loops.

To a greater extent than most knitted fabrics, fiberglass knits tend to cuff or fray at a cut edge as the yarns are severed and adjacent loops unravel. Fraying and raveling produce unsightly ends and, in the case of an orthopedic cast, frayed ends may interfere with the formation of a smooth cast, and loose, frayed ends may be sharp and irritating after the resin thereon has cured. Accordingly, frayed edges are considered a distinct disadvantage in orthopedic casting tapes. Stretchy fiberglass fabrics which resist fraying are disclosed in U.S. Pat. No. 4,609,578 (Reed), the disclosure of which is incorporated by reference for its teaching of heat-setting. Thus, it is well known that fraying of fiberglass knits at cut edges can be reduced by passing the fabric through a heat cycle which sets the yarns giving them new three-dimensional configurations based on their positions in the knit. When a fiberglass fabric which has been heat-set is cut, there is minimal fraying and when a segment of yarn is removed from the heat-set fabric and allowed to relax, it curls into the crimped shape in which it was held in the knit. Accordingly, at the site of a cut, the severed yarns have a tendency to remain in their looped or knotted configuration rather than to spring loose and cause fraying.

In processing extensible fiberglass fabrics according to U.S. Pat. No. 4,609,578 (Reed), a length of fabric is heat-set with essentially no tension. The fabric is often wound onto a cylindrical core so large batches can be processed at one time in a single oven. Care must be taken to avoid applying undue tension to the fabric during wind-up on the knitter which would distort the knots and loops. To prevent applying tension to the fabric during winding, the winding operation is preferably performed with a sag in the fabric as it is wound on the core.

Alternatively, U.S. Pat. No. 5,014,403 (Buese) describes a method of making a stretchable orthopedic fiberglass casting tape by knitting an elastic yarn under tension into the fiberglass fabric in the length direction, releasing the tension from the elastic yarn to compact the fabric and removing the elastic yarn from the fabric. The resulting fabric must then be collected under low tension in order to preserve the compact form. Likewise, any subsequent heat setting must also be performed under low tension. However, to avoid exceeding this low tension is difficult and as a result substantial amounts of the compaction imparted by the elastomeric yarn may be lost during subsequent processes. The elastic yarn is removed by a combustion process which may cause localized areas of high temperature which may degrade the fiberglass yarns. The physical properties of glass fibers are adversely affected when subjected to temperatures in excess of about 540° C. Heating fiberglass fabrics to temperatures above about 540° C. should be avoided, as subjecting the fiberglass to temperatures of greater than about 540° C. can weaken the fiberglass yarns in the fabric, which may result in reduced strength of casts made from such fabrics.

From the foregoing, it will be appreciated that what is needed in the art is an orthopedic casting material which has both the advantages of plaster of Pads, e.g., good moldability and palpability of the fine bone structure, and the advantages of non-plaster of Pads materials, e.g., good strength-to-weight ratio and good air permeability. In this regard it would be a significant advancement in the art to provide such a combination of advantages without actually using plaster of Paris, thereby avoiding the inherent disadvantages of plaster of Paris outlined herein. It would be a further advancement in the art to provide such non-plaster of Paris orthopedic casting materials which have as good or better properties than the non-plaster of Paris orthopedic casting materials of the prior art. Such orthopedic casting materials and methods for preparing the same are disclosed and claimed herein.

RELATED APPLICATIONS

Of related interest are the following U.S. Patent Applications, filed on Jan. 25, 1993 by the assignee of this invention: "Mechanically Compacted Fabrics for Orthopedic Casting Tapes"—Ser. No. 08/008,161, now U.S. Pat. No. 5,382,445; and "Microcreping of Fabrics for Orthopedic Casting Tapes"—Ser. No. 08/008,751; and U.S. Patent Application filed on even date herewith by the assignee of this invention entitled "Wet Compacting of Fabrics for Orthopedic Casting Tapes"—Ser. No. 08/142,573, now U.S. Pat. No. 5,370,927, and "Vibration Compacted Fabrics for Orthopedic Casting Tapes, Ser. No. 08/142,177, which are herein incorporated by reference.

SUMMARY OF THE INVENTION

The present invention provides an article comprising a compacted fiberglass fabric sheet and a curable or hardenable resin coated onto the fabric sheet. The fabric sheet is compacted using a heat shrinkable yarn (hereinafter "heat shrink yarn") and is optionally heat set thereby removing the heat shrink yarn and providing extensibility to the fabric. The article may be in the form of an orthopedic bandage. The present invention also provides an article comprising a compacted fiberglass fabric sheet, a heat shrink yarn, and a curable or hardenable resin coated onto the fabric sheet. The heat shrink yarn in this embodiment remains in the fabric, thereby providing resistance to lengthwise extension, yet yields in response to a tensile force thereby providing a controlled extension of the fabric.

DETAILED DESCRIPTION OF THE INVENTION

Figure 1:
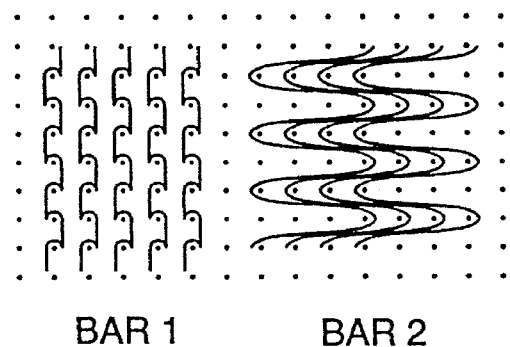
FIG. 1 is a two bar Raschel knit in which bar one performs a simple chain stitch and bar two performs lapping motions to lay in yarn.

The present invention relates to orthopedic casting materials and methods for preparing and using such orthopedic casting materials, wherein the materials comprise a fiberglass backing or fabric which is impregnated with a curable or hardenable liquid resin. In particular, the fabrics employed in the present invention have important characteristics and physical properties which allow the fabrics to be made highly extensible.

One element of this invention is a flexible sheet upon which a curable or hardenable resin can be coated to reinforce the sheet when the resin is cured or hardened thereon. The sheet is preferably porous such that the sheet is at least partially impregnated with the resin. Examples of suitable sheets are knit fabrics comprised of inorganic fibers or materials such as fiberglass. It is presently believed that this process will work for a variety of high modulus materials including fiberglass, ceramic fibers such a Nextel™, and polyaramides fibers such as Kevlar. The sheet may alternatively be referred to as the "scrim" or the "backing."

The term "high modulus" as used herein to describe the fabric component of the casting material refers to the degree of resistance to deformation or bending and is expressed in terms of the modulus of elasticity. Modulus of elasticity is the ratio of change in stress to the change in strain which occurs when a fiber is mechanically loaded. The initial modulus of elasticity of the fiber should be greater than about $8 \times 10^6$ lbs/square inch (55.2 GPa). Such fibers include continuous filament E-fiberglass, polyaramid filament known as Kevlar® 49 (available from E. I. DuPont de Nemours and Company), ceramic fibers such as Nextel® (available from 3M Company), continuous filament graphite such as Thornel® (available from Union Carbide Corp.), boron fiber (such as made by Avco Corp.), and metal fibers such as stainless steel filaments which when fine enough can be formed into fabrics by weaving or knitting. These high modulus fibers impart a high degree of strength and rigidity to the cast. They may be combined with low to intermediate modulus materials when the flexibility of such yarns enables easier fabrication of the fabric. Low modulus fibers are those having an initial modulus of elasticity of less than about $3 \times 10^6$ lbs/in$^2$ (20.7 GPa) and include cotton, polyester (such as "Dacron"), polypropylene, "Orlon", "Dynel"® (Union Carbide), "Nomex"® (Dupont) and nylon.

The present invention involves compacting a fabric sheet using a heat shrink yarn to impart stretchability and conformability to the fabric while minimizing undesirable recovery forces.

Suitable fabrics, after compaction, have important characteristics and physical properties which allow the fabrics to be loaded with resin to the extent needed to provide proper strength as an orthopedic casting material, while providing necessary porosity as well as improved extensibility leading to improved conformability, tactile manipulability, moldability, and palpability. Several important criteria for choosing a fabric which will provide the characteristics necessary for purposes of the present invention include: (1) lengthwise extensibility and conformability after compaction, and the related characteristics of moldability, tactility, and palpability once the fabric has been resin impregnated; (2) resin loading capacity; and (3) porosity. It is important that each of these parameters be carefully controlled in providing fabrics which will successfully form orthopedic casting materials (e.g., casts having high strength and good layer-to-layer lamination strength) within the scope of the present invention.

Extensibility is important from the standpoint that the fabric must be extensible enough along its length, i.e., in the elongated direction, so that the resultant orthopedic casting material can be made to substantially conform to the body part to which it is applied. Materials which are not sufficiently extensible in the elongated direction do not conform well to the body part when wrapped therearound, often resulting in undesirable wrinkles or folds in the material. On the other hand, the extensibility of the fabric in the elongated direction should not be so high that the material is too stretchy, resulting in a material structure which may be deformed to the extent that strength is substantially reduced.

For purposes of the present invention, the coated fabric, after compaction and after being coated with a curable liquid resin, should have from about 10% to about 200% extensibility in the elongated direction when a 2.63N tensile load or force is applied per 1 cm wide section of the fabric, and preferably from about 25% to about 100% extensibility in the elongated direction when a 2.63N tensile load or force is applied per 1 cm wide section of the fabric, and more preferably from about 35% to about 65% extensibility in the elongated direction when a 268 gram load or force is applied across a 1 cm section of the fabric.

Although not nearly as critical, it is also desirable that the fabric employed have some extensibility along its width, i.e., in the direction transverse to the elongated direction. Thus although the fabric may have from 0% to 100% extensibility in the transverse direction, it is presently preferable to use a fabric having from about 1% to about 30% extensibility in the transverse direction when a 2.63N tensile load or force is applied per 1 cm wide section of the fabric. The compaction process described herein principally imparts extensibility in the elongated direction. However, it is anticipated that one might compact a fabric in the elongated direction and in the transverse direction, thereby imparting biaxial extensibility.

The fabrics of the present invention, after compaction, although stretchable, are preferably not overly elastic or resilient. Fabrics which are overly elastic, when used as backings for orthopedic bandages, tend to cause undesirable constriction forces around the wrapped limb or body part. Thus, once the resin impregnated fabric has been stretched and applied around a body part, the stretched material preferably maintains its shape and does not resort back to its unstretched position.

The resin loading capacity or ability of the fabric to hold resin is important from the standpoint of providing an orthopedic casting material which has sufficient strength to efficaciously immobilize a body part. The surface structure of the fabric, including the fibers, interstices, and apertures, is very important in providing proper resin loading for purposes of the present invention. In this regard, the interstices between the fibers of each fiber bundle must provide sufficient volume or space to hold an adequate amount of resin within the fiber bundle to provide the strength necessary; while at the same time, the apertures between fiber bundles preferably remain sufficiently unoccluded such that adequate porosity is preserved once the cast is applied. Thus, the interstices between fibers are important in providing the necessary resin loading capacity, while the apertures are important in providing the necessary porosity for the finished cast. However, a balancing of various parameters is needed to achieve both proper resin loading and porosity. The coated fabric should have preferably between about 6 and 70 openings (i.e., apertures) per square cm, more preferably between about 10 and 50 openings per square cm, and most preferably between about 20 and 40 openings per square cm when measured under a tensile load of 2.63N/cm width. As used herein an "opening" is defined as the area defined by adjacent wales and in-lay members. The number of openings per unit area is therefore determined by multiplying the number of wales by the number of courses and dividing by the area.

As used herein, a "compacted" fiberglass sheet is one in which extensibility is imparted to the fabric due to the structural overlapping of successive loops and/or the structural relaxation of loops by the "heat shrink yarn" compaction processes described herein. The compaction process is believed to impart extensibility to the fabric by "compacting" the loops of the knit as described herein. Typically, when a fabric is knitted the inside surfaces of two adjacent rows of loops are in contact or nearly in contact and the loops are distorted in the lengthwise direction (e.g., in the shape of an oval). This contact and/or distortion is the result of the fabric being under tension while the knit is being formed. Each successive row of loops (i.e., chain stitches) is, in effect, formed against the preceding row of loops. The compaction process of the present invention imparts fabric compaction by overlapping adjacent rows of loops (i.e., to a "non-contacting" position) and/or relaxing the strained loops to a lower stress (e.g., more circular) configuration and optionally setting or annealing the fabric in the compacted form. Extensibility is imparted to the fabric due to the overlap of the rows and/or the greater ability of the more circular loops to be deformed. When tension is again applied to the fabric the loops can return to their original "contacting" position, i.e., the position they occupied when originally knit.

Fiberglass knitted fabrics with good extensibility are achievable with two common knitting methods: Raschel and tricot. Raschel knitting is described in "Raschel Lace Production" by B. Wheatley (published by the National Knitted Outerwear Association, 51 Madison Avenue, New York, N.Y. 10010) and "Warp Knitting Production" by Dr. S. Raz (published by Heidelberger Vedagsanstadt und Druckerei GmbH, Hauptstr. 23, D-6900 Heidelberg, Germany). Two, three and four bar Raschel knits can be produced by regulating the amount of yarn in each stitch. Orthopedic casting tape fabrics are generally two bar Raschel knits although extra bars may be employed. Factors which affect the extensibility of fiberglass Raschel knits are the size of the loops in the "chain" stitch, especially in relation to the diameter(s) of the yarn(s) which passes through them, and the amount of a loose yarn in the "laying" or "laid-in" stitch(es). If a chain loop is formed and two strands of lay-in yarn pass through it which nearly fill the loop, then the loop resists deformation and little stretch will be observed. Conversely, if the lay-in yarns do not fill the loop, then application of tension will deform the loop to the limits of the lay-in yarn diameter and stretch will be observed.

Typical bar patterns for the knit fabric substrates of the present invention are shown in the drawings.

FIG. 1 is a two bar Raschel knit in which bar one performs a simple chain stitch and bar two performs lapping motions to lay in yarn.

Figure 2:
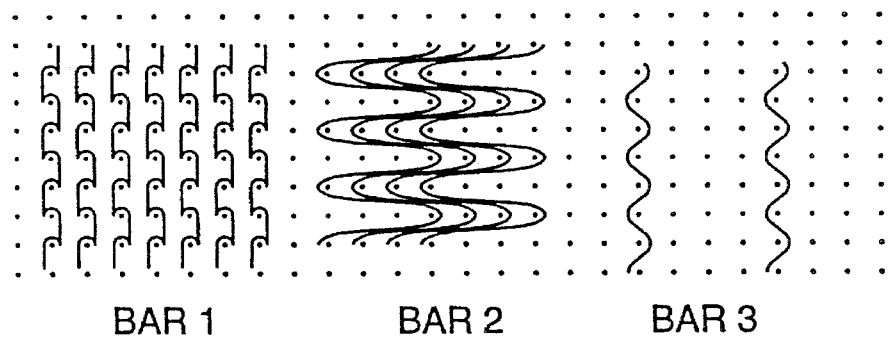
FIG. 2 is a three bar Raschel knit in which bar one performs a simple chain stitch and bars two and three perform lapping motions to lay in yarn, and wherein bar three illustrates the lay in of a heat shrink yarn.

FIG. 2 is a three bar Raschel knit in which bar one performs a simple chain stitch and bars two and three perform lapping motions to lay in yarn, and wherein bar three illustrates the lay in of a heat shrink yarn.

Figure 3:
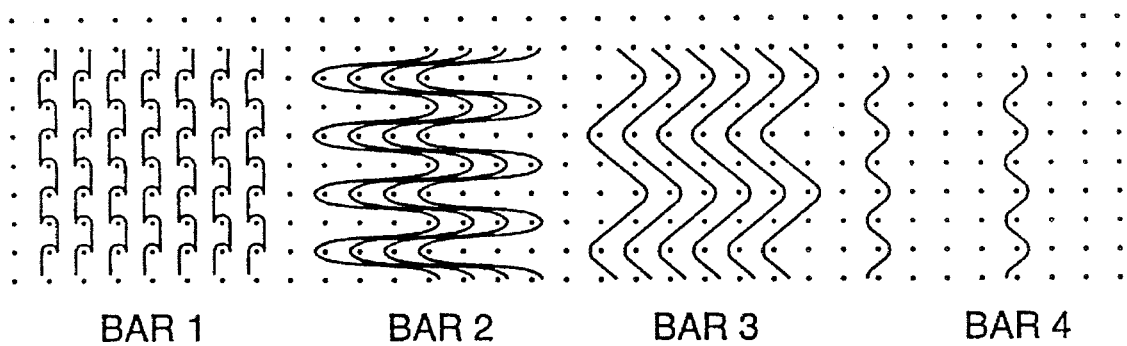
FIG. 3 is a four bar Raschel knit in which bar one performs a simple chain stitch and bars two, three and four perform lapping motions to lay in yarn, and wherein bar four illustrates the lay in of a heat shrink yarn.

FIG. 3 is a four bar Raschel knit in which bar one performs a simple chain stitch and bars two, three and four perform lapping motions to lay in yarn, and wherein bar four illustrates the lay in of a heat shrink yarn.

Figure 4:
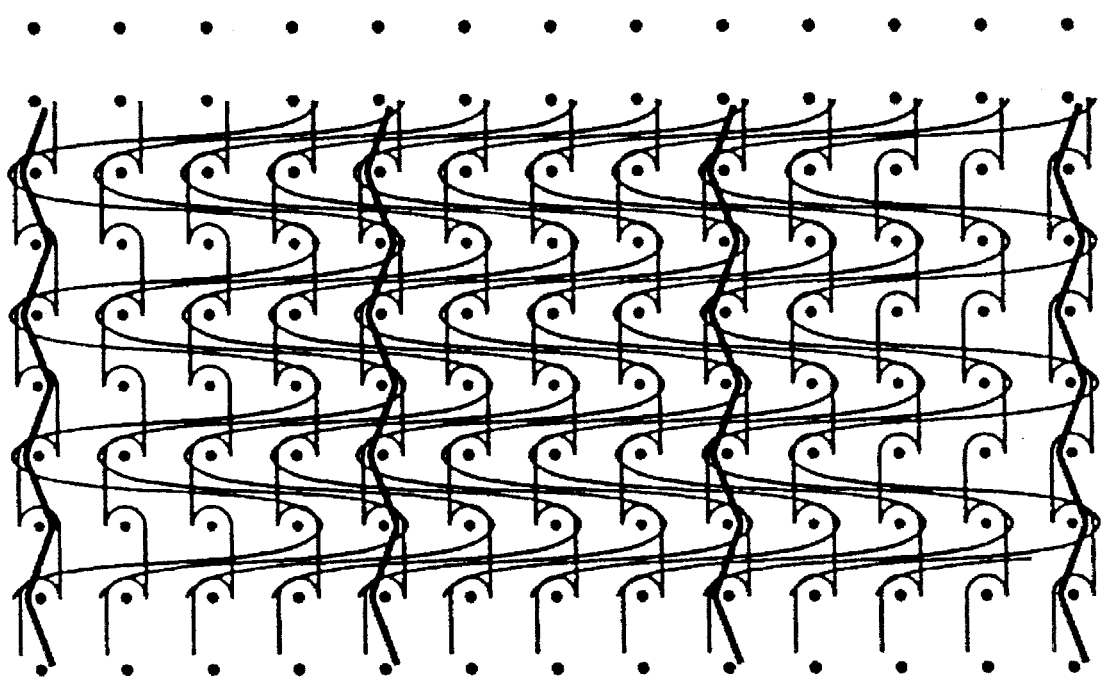
FIG. 4 is a depiction of a three bar Raschel knit in which bar one performs a simple chain stitch, bar two performs lapping motion to lay in yarn, and bar three performs lapping motions to lay in a heat shrink yarn. The bars are depicted in a overlapping view.

FIG. 4 is a depiction of a three bar Raschel knit in which bar one performs a simple chain stitch, bar two performs lapping motion to lay in yarn, and bar three performs lapping motions to lay in a heat shrink yarn. The bars are depicted in a overlapping view.

Figure 5:
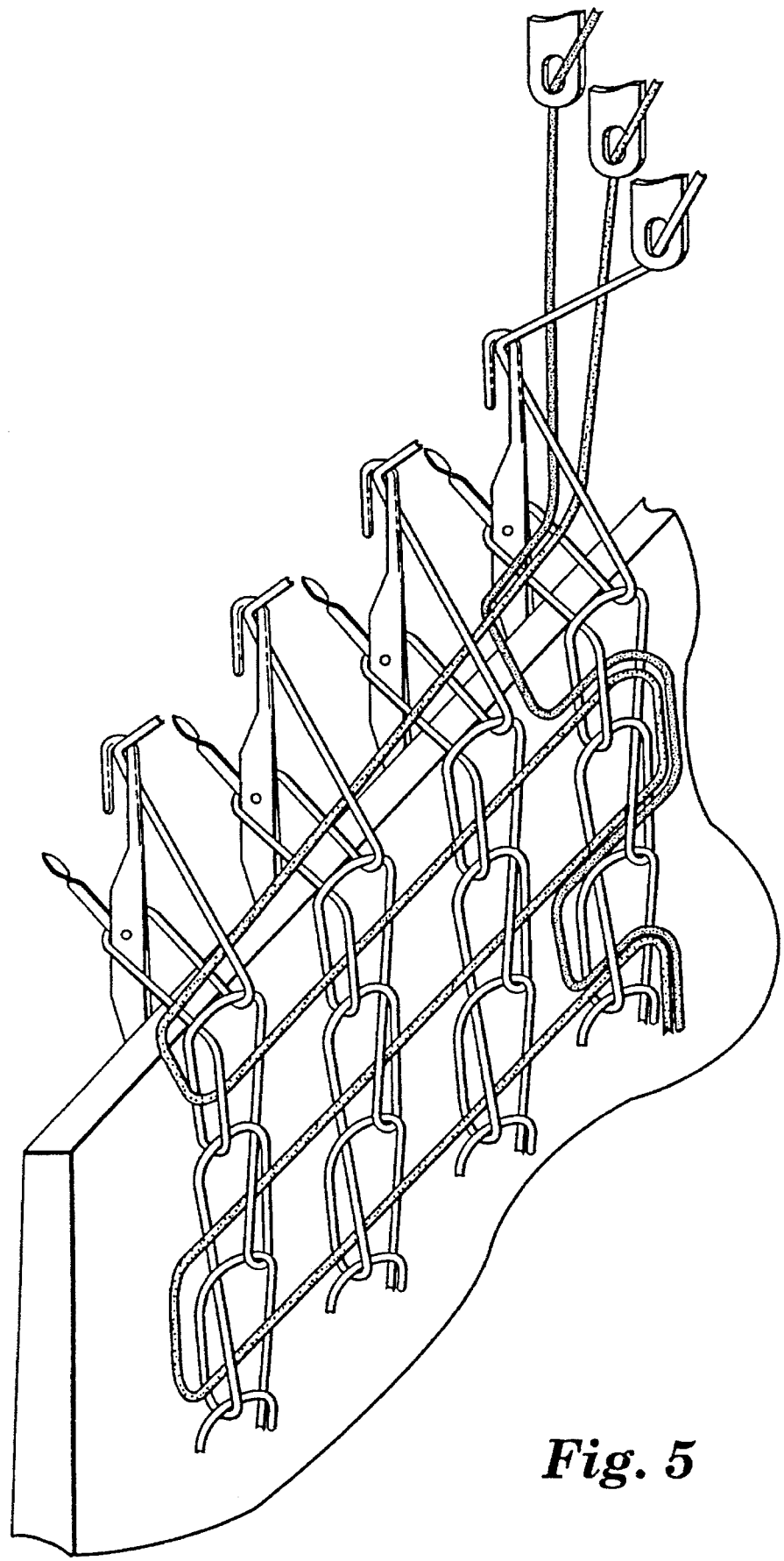
FIG. 5 is a depiction of a three bar "latch hook" Raschel knitter in which four needles are shown knitting four chain stitches and two guidebars providing lay-in yarns. For the purposes of this invention, one might alternatively employ a "compound needle" Raschel knitter which is not shown.

FIG. 5 is a depiction of a three bar "latch hook" Raschel knitter in which four needles are shown knitting four chain stitches and two lay-in stitches. For the purposes of this invention, one might alternatively employ a "compound needle" Raschel knitter which is not shown.

It should be understood that the above bar patterns may be modified. For example, FIG. 2 may be modified by employing fewer or more heat shrink lay-in yarns. Alternatively, the heat shrink yarn may be knitted in one or more of the chain stitches of the fabric or more than one heat shrink yarns may be laid in a single chain stitch.

For orthopedic casting material, the fabric selected (preferably fiberglass), in addition to having the extensibility requirement noted above, should be of a suitable thickness and mesh size to insure good penetration of the curing agent (e.g., water) into the roll of resin-coated tape and to provide a finished cast with adequate strength and porosity. Such fabric parameters are well-known to those skilled in the art and are described in U.S. Pat. No. 4,502,479 which is herein incorporated by reference.

When the casting material is a fiberglass fabric, suitable heat shrink yarns are made of fibers which shrink and optionally combust at temperatures lower than the degradation temperature of the inorganic fibers (e.g., glass fibers) of the fabric. Preferably the shrinkage and combustion temperatures of the heat shrink yarn are less than or equal to the temperature commonly used for heat setting fiberglass yarns. More preferably the shrinkage temperature of the heat shrink yarn is between about 70° C. and 300° C. Most preferably the shrinkage temperature of the heat shrink yarn is between about 100° C. and 200° C. Preferably the combustion temperature of the heat shrink yarn is between about 200° C. and 540° C. More preferably the combustion temperature of the heat shrink yarn is between about 300° C. and 500° C. Heating the fabric to temperatures above about 540° C. should be avoided as subjecting the fiberglass to temperatures of greater than about 540° C. can weaken the fiberglass yarns in the fabric which may result in reduced strength of casts made from such fabrics.

Suitable heat shrink yarns for use in the present invention include yarns which shrink when heated at a temperature less than the degradation temperature of the inorganic fabric and which when present in a sufficient quantity are capable of compacting the fabric. Preferred heat shrink yarns comprise fibers having at least 10% shrinkage when heated (and when tested using a Testrite MK4 tester as described in Example 1). More preferably, the yarn has at least 20% shrinkage and most preferably at least 30% shrinkage.

One class of suitable heat shrink yarns are partially or highly oriented polymer yarns which shrink when heated above their glass transition temperature but below their melting temperature. In general, the physical properties of polymer fibers (e.g., polyester fibers) is strongly affected by fiber structure. For example, to provide the heat shrink property some degree of crystallinity is preferred.

Suitable polymer fibers for use as the heat shrink yarn include both multifilament and monofilament (staple or continuous filament) yarns which are optionally texturized and fully or partially oriented. The yarns may be comprised of semi-crystalline polymers such as polyester, polyamide, polyethylene and copolymers or graft copolymers of these. Preferred polymer fibers for use as the heat shrink yarn include polyester and polyethylene. Partially oriented polyester is presently most preferred.

The heat shrink yarn(s) may be knit into the fabric either as a lay-in or as a chain stitch. Preferably, the heat shrink yarn is knit into the fabric as a lay-in stitch. The essential requirements of a heat shrink yarn are that it be capable of knitting with the fabric yarn and that it compact the fabric. Therefore, when the heat shrink yarn is shrunk and optionally combusted, e.g., through application of heat, the fabric remains present in the form of a compacted, optionally heat set fabric. The heat shrink yarn is preferably knit into the fabric such that the knit is compacted at least 10%, more preferably at least 14%, and most preferably at least 18%.

When the heat shrink yarn is present as laid-in yarns it is preferably knitted through a single wale. This embodiment is illustrated, for example, in FIG. 2. In that figure, a third bar is depicted knitting a heat shrink yarn across a single chain stitch (bar 1). Additional lay-in yarns are knitted into the fabric using bar 2. In this manner maximum lengthwise compaction may be achieved as the heat shrink yarn is shrunk. Alternatively, the heat shrink yarn may cross more than one wale. It is believed that this embodiment will produce a fabric with biaxial compaction.

As previously mentioned, the heat shrinkable yarn should be positioned in the knit so as to minimize the amount required and maximize the force generated during contraction. If the yarn is placed in as a wale in addition to the fiberglass wales (i.e., as an additional wale since after desizing some wales would need to be present) a significant amount of organic material is added which could result in a brittle tape after heat treatment. If the yarn is placed as a lay-in and maximum lengthwise compaction is desired then the yarn is preferably laid in across a single needle in order to ensure that most of the shrinkage force of the laid-in yarn is used to compact the tape in the length direction.

The heat shrink yarn may be knitted through each wale (not shown in FIG. 2) or through fewer than all the wales (as shown in FIG. 2). Notably, there need not be a heat shrink yarn for every wale. The heat shrink yarn need only be present in the fabric in an amount sufficient to give the desired compaction to the fabric when the yarn is heat shrunk. It has been found that knitting the heat shrink yarn through every fourth or fifth wale is preferred. Having too many heat shrink yarns increases the potential for undesirable localized heating of the fiberglass during the optional combustion step. Having too few heat shrink yarns results in uneven compaction or inadequate compaction. The exact number of heat shrink yarns needed will depend upon the fabric weight and knit pattern employed, the weight and shrink properties of the heat shrink yarn employed, and the desired amount of compaction.

The heat shrink yarn may also be in the form of a chain stitch yarn. When the heat shrink yarn is knitted in the form of a chain stitch it is preferable to lay in noncombustible yarns (e.g., fiberglass yarns) across the heat shrink chain stitch yarn and thereby connect adjacent noncombustible chain stitches. Thus, if the heat shrink chain stitch is later optionally removed when heat setting the fiberglass, the fabric will maintain its integrity.

It may also be beneficial to vibrate the fabric during the compaction process to improve the uniformity of the compaction. This is particularly important when the heat shrink yarns are spaced apart and not knit through every wale. Suitable vibration methods are described in copending U.S. Patent Application "Vibration Compacted Fabrics for Orthopedic Casting Tapes", Ser. No. 08/142,177.

In processing the knitted fiberglass fabric of the present invention, a length of fabric is optionally, and preferably, heat-set while the fabric is in a compacted form. Preferably, the fabric is compacted and then wound onto a cylindrical core so large batches can be heat set at one time in a single oven. Care must be taken to avoid applying undue tension to the fabric (after combustion of the heat shrink yarn and before the heat set has occurred) which would distort the knots and loops.

A continuous heat-setting process may also be used in which a length of fabric is first compacted by heat shrinking the heat shrink yarn and then the compacted fabric is placed on a moving conveyor system and passed through an oven for a sufficient time and temperature to achieve heat setting of the fabric. Alternatively, one may use the same oven to both compact the fabric and heat set the fiberglass yarns provided that sufficient time is allowed for the compaction process prior to melting of the heat shrink yarn. Notably, when short lengths of fabric are so processed the ends of the heat shrink yarn should be held in relation to the ends of the fiberglass yarns so as to cause compaction. Otherwise the heat shrink yarns may merely slip against the fabric as they shrink and not cause compaction of the knit fabric.

The heat-setting step may be performed in a number of conventional ways known to the art. In heat-setting a small piece of fiberglass fabric, e.g., 25 centimeters of tape, in a single layer, a temperature of 425° C. for three minutes has been found to be sufficient. Equivalent setting at lower temperatures is possible, but longer time is required. In general, batch processes require a longer residence time at the selected temperature due to the mass of glass fabric which must be heated and the need to remove all traces of sizing material which may undesirably color the final fabric.

The optimum heat-setting process described above is sufficient in most cases to remove the sizing from the fabric. However, the process of the present invention may also be practiced using partially heat-desized or a chemically-desized fabric. Chemical desizing processes are described in U.S. Pat. Nos. 3,686,725; 3,787,272; and 3,793,686. Heat desizing processes are described in U.S. Pat. No. 4,609,578.

In general, to completely desize the fiberglass tape and not leave any visible residue it is necessary to heat the tape to a temperature between 370° and 430° C., more preferably between 400° and 430° C. The closer you get to 430° C. the shorter the cycle and more efficient the operation. Although the tape could be cleaned at higher temperatures, this may cause permanent degradation of the fiberglass fabric. For example, when the temperature of the fabric exceeds 480° C. and especially when the temperature exceeds 540° C. the tensile strength of the knit decreases very rapidly. When the tape is exposed to temperatures over 590° C. it becomes very brittle and wrapping a cast using normal tension is precluded. A preferred heat desizing cycle raises the oven temperature to about 430° C. and maintains that temperature until the tape is clean (e.g., about 6–8 hours in a recirculating oven). However, obtaining this result is somewhat complicated since the tape's temperature is affected by both the heat of the oven and the heat of combustion resulting from burning the sizing and/or any organic yarn (i.e., the heat shrink yarn) which may be present.

Controlling the exotherm from organic material in the knit is essential and can be accomplished most easily and economically by limiting the total amount of added organic material (e.g., sizing and heat shrink yarn) which must be removed. In order to knit a fiberglass yarn without excessive damage a sizing is preferably present. Preferably the amount of sizing utilized is the minimum level necessary to prevent damage during knitting. A preferred amount of sizing on fiberglass is between 0.75 and 1.35% (based on weight of the fabric). In addition to this sizing, in order to compact the tape, a heat shrinkable yarn is added to the fabric. Since this yarn adds substantially to the total level of organic material in the fabric it is important to limit the amount added. This can be accomplished by several methods.

First, one may limit the number of heat shrink yarns used. Initial trials at compacting fabrics using the method of the present invention placed the heat shrink yarn in every wale. This amount of heat shrink yarn is believed to be unnecessary and undesirable due to the resulting high exothermic temperature during desizing. Preferably the knit has a heat shrinkable yarn in-laid across the tape only in wales spaced 2–6 needles apart. Most preferably the knit has a heat shrinkable yarn in-laid across the tape only in wales spaced 3 to 6 needles apart. Normally, the spacing is uniform across the web but since the preferred pattern used crosses only a single needle it can be varied without modification to the knitting machine.

Second, one may decrease the denier of the heat shrink yarn. Preferably, the lowest denier yarn which has sufficient shrink force to compact the tape should be used. For preferred fiberglass fabrics the preferred heat shrink yarns are about 100 to 500 denier, more preferably about 200 to 300 denier.

Finally, it has been observed that the jumbo's winding tension can greatly influence the exothermic temperature rise due to combustion and therefore adversely affect web integrity. In general, jumbos wound under higher tension tend to reach a lower peak temperature and have a greater web integrity than those wound more loosely. It is believed that the organic content of more tightly wound jumbos burn more slowly and therefore the jumbos have lower peak internal temperatures. While not intending to be bound by theory, this result is believed to be due to oxygen starvation within the jumbo. Within a jumbo (i.e., away from the surface of the roll) the availability of oxygen is controlled by the diffusion rate into the jumbo. Careful control of the roll's permeability to oxygen can be utilized to control the rate of combustion of the organic material.

The fabric is preferably cooled prior to application of the resin. The resin selected to apply to the heat-set fabric is dictated by the end-use of the product. For orthopedic casting materials, suitable resins are well-known and described for example, in U.S. Pat. Nos. 4,376,438; 4,433,680; 4,502,479; and 4,667,661 and U.S. patent application Ser. No. 07/376,421 which are herein incorporated by reference. The presently most preferred resins are the moisture-curable isocyanate-terminated polyurethane prepolymers described in the aforementioned patents. Alternatively, one may employ one of the resin systems described herein. The amount of such resin applied to the fiberglass tape to form an orthopedic casting material is typically an amount sufficient to constitute 35 to 50 percent by weight of the final "coated" tape. The term "coated" or "coating" as used herein with respect to the resin refers generically to all conventional processes for applying resins to fabrics and is not intended to be limiting.

To insure storage stability of the coated tape, it must be properly packaged, as is well known in the art. In the case of water-curable isocyanate-terminated polyurethane prepolymer resin systems, moisture must be excluded. This is typically accomplished by sealing the tape in a foil or other moistureproof pouch.

In one embodiment of the present invention, a fiberglass fabric which further comprises a plurality of heat shrink yarns is knit according to the process described herein, compacted by heat shrinking the aforementioned yarns, and then heat set in the compacted form while also removing the heat shrink yarns. The compacted fabric is then coated with a curable resin. There are many advantages to this process over conventional knitting processes. First, unlike traditional uncompacted knit fiberglass fabrics, the fabric produced by this method has increased extensionability. Furthermore, the heat shrink yarn, when in its shrunken state, provides support to the fabric during subsequent collecting operations (such as when winding a large jumbo roll) thereby preventing undesirable extension of the fabric prior to it being heat set. The finished fabric of this embodiment comprises only noncombustible yarns and retains its compacted form as a result of the heat setting of the fiberglass yarns.

In a second embodiment of the present invention, a fiberglass fabric which further comprises a plurality of heat shrink yarns is knit according to the process described herein and compacted by heat shrinking the aforementioned yarns. The compacted fabric is then coated with a curable resin. There are many advantages to this process over conventional knitting processes. First, unlike traditional uncompacted knit fiberglass fabrics, the fabric produced by this method has increased extensibility. The heat shrink yarn, when in its shrunken state, provides support to the fabric during subsequent winding operations (such as when winding a roll during the production process) and unwinding operations (such as when the fabric is applied to the patient) thereby preventing undesirable extension of the fabric prior to it being applied. The finished fabric of this embodiment retains its compacted form principally as a result of the heat shrink yarns and is extensible only when the heat shrink yarns are plastically deformed (e.g., by stretching them). That is to say, the fiberglass fabric may be extended, as needed, when it is applied to the patient by stretching (and thereby plastically deforming) the heat shrunken yarns. In contrast to stretching an elastic yarn, plastically deforming a heat shrink yarn avoids undesirable rebound of the fabric which could cause undesirable constriction forces. Rather, the plastically deformed heat shrink yarns retain their deformed state when the tensile force is removed.

Suitable fabrics, after compaction, are compacted to between about 30 and 90 percent of their original dimension. More preferably, the fabric is compacted to between about 50 and 80 percent of its original dimension. Most preferably, the fabric is compacted to between about 60 and 75 percent of its original dimension.

The curable or hardenable resins useful in this invention are resins which can be used to coat a sheet material and which can then be cured or hardened to reinforce the sheet material. For example, the resin is curable to a crosslinked thermoset state. The preferred curable or hardenable resins are fluids, i.e., compositions having viscosities between about 5 Pa s and about 500 Pa s, preferably about 10 Pa s to about 100 Pa s.

The resin used in the casting material of the invention is preferably any curable or hardenable resin which will satisfy the functional requirements of an orthopedic cast. Obviously, the resin must be nontoxic in the sense that it does not give off significant amounts of toxic vapors during curing which may be harmful to either the patient or the person applying the cast and also that it does not cause skin irritation either by chemical irritation or the generation of excessive heat during cure. Furthermore, the resin must be sufficiently reactive with the curing agent to insure rapid hardening of the cast once it is applied but not so reactive that it does not allow sufficient working time to apply and shape the cast. Initially, the casting material must be pliable and formable and should adhere to itself. Then in a short time following completion of cast application, it should become rigid or, at least, semi-rigid, and strong to support loads and stresses to which the cast is subjected by the activities of the wearer. Thus, the material must undergo a change of state from a fluid-like condition to a solid condition in a matter of minutes.

The preferred resins are those cured with water. Presently preferred are urethane resins cured by the reaction of a polyisocyanate and a polyol such as those disclosed in U.S. Pat. No. 4,131,114. A number of classes of water-curable resins known in the art are suitable, including polyurethanes, cyanoacrylate esters, epoxy resins (when combined with moisture sensitive catalysts), and prepolymers terminated at their ends with trialkoxy- or trihalo-silane groups. For example, U.S. Pat. No. 3,932,526 discloses that 1,1-bis(perfluoromethylsulfonyl)-2-aryl ethylenes cause epoxy resins containing traces of moisture to become polymerized.

Resin systems other than those which are water-curable may be used, although the use of water to activate the hardening of an orthopedic casting tape is most convenient, safe and familiar to orthopedic surgeons and medical casting personnel. Resin systems such as that disclosed in U.S. Pat. No. 3,908,644 in which a bandage is impregnated with difunctional acrylates or methacrylates, such as the bis-methacrylate ester derived from the condensation of glycidyl methacrylate and bisphenol A (4,4'-isopropylidenediphenol) are suitable. The resin is hardened upon wetting with solutions of a tertiary amine and an organic peroxide. Also, the water may contain a catalyst. For example, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system). The strength, rigidity and rate of hardening of such a bandage is subjected to the factors disclosed herein. Alternatively, hardenable polymer dispersions such as the aqueous polymer dispersion disclosed in U.S. Pat. No. 5,169,698, which is herein incorporated by reference, may be used in the present invention.

Some presently more preferred resins for use in the present invention are water-curable, isocyanate-functional prepolymers. Suitable systems of this type are disclosed, for example, in U.S. Pat. No. 4,411,262, and in U.S. Pat. No. 4,502,479. Preferred resin systems are disclosed in U.S. Pat. No. 4,667,661 and U.S. patent application Ser. No. 07/376, 421. The following disclosure relates primarily to the preferred embodiment of the invention wherein water-curable isocyanate-functional prepolymers are employed as the curable resin. A water-curable isocyanate-functional prepolymer as used herein means a prepolymer derived from polyisocyanate, preferably aromatic, and a reactive hydrogen compound or oligomer. The prepolymer has sufficient isocyanate-functionality to cure (i.e., to set or change from a liquid state to a solid state) upon exposure to water, e.g., moisture vapor, or preferably liquid water.

It is preferred to coat the resin onto the fabric as a polyisocyanate prepolymer formed by the reaction of an isocyanate and a polyol. Suitable isocyanates include 2,4-toluene diisocyanate, 2,6-toluene diisocyanate, mixture of these isomers, 4,4'-diphenylmethane diisocyanate, 2,4'-diphenylmethane diisocyanate, mixture of these isomers together with possible small quantities of 2,2'-diphenylmethane diisocyanate (typical of commercially available diphenylmethane diisocyanate), and aromatic polyisocyanates and their mixtures such as are derived from phosgenation of the condensation product of aniline and formaldehyde. It is preferred to use an isocyanate which has low volatility such as diphenylmethane diisocyanate (MDI) rather than a more volatile material such as toluene diisocyanate (TDI). Typical polyols for use in the prepolymer system include polypropylene ether glycols (available from Arco Chemical Co. under the trade name Arcol™ PPG and from BASF Wyandotte under the trade name Pluracol™), polytetramethylene ether glycols (Polymeg™ from the Quaker Oats Co.), polycaprolactone diols (Niax™ PCP series of polyols from Union Carbide), and polyester polyols (hydroxyl terminated polyesters obtained from esterification of dicarboxylic acids and diols such as the Rucoflex™ polyols available from Ruco division, Hooker Chemical Co.). By using high molecular weight polyols, the rigidity of the cured resin can be reduced.

An example of a resin useful in the casting material of the invention uses an isocyanate known as Isonate™ 2143L available from the Upjohn Company (a mixture containing about 73% of MDI) and a polypropylene oxide polyol from Arco known as Arcol™ PPG725. To prolong the shelf life of the material, it is preferred to include from 0.01 to 1.0 percent by weight of benzoyl chloride or another suitable stabilizer.

The reactivity of the resin once it is exposed to the water curing agent can be controlled by the use of a proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using 4-[2-[1-methyl-2-(4-morpholinyl)ethoxy]ethyl]morpholine (MEMPE) prepared as described in U.S. Pat. No. 4,705,840, the disclosure of which is incorporated by reference, at a concentration of about 0.05 to about 5 percent by weight.

Foaming of the resin should be minimized since it reduces the porosity of the cast and its overall strength. Foaming occurs because carbon dioxide is released when water reacts with isocyanate groups. One way to minimize foaming is to reduce the concentration of isocyanate groups in the prepolymer. However, to have reactivity, workability, and ultimate strength, an adequate concentration of isocyanate groups is necessary. Although foaming is less at low resin contents, adequate resin content is required for desirable cast characteristics such as strength and resistance to peeling. One satisfactory method of minimizing foaming is to add a foam suppressor such as silicone Antifoam A (Dow Corning), or Antifoam 1400 silicone fluid (Dow Corning) to the resin. It is especially preferred to use a silicone liquid such as Dow Corning Antifoam 1400 at a concentration of about 0.05 to 1.0 percent by weight. Water-curable resins containing a stable dispersion of hydrophobic polymeric particles, such as disclosed in U.S. patent application Ser. No. 07/376,421 and laid open as European Published Patent Application EPO 0 407 056, may also be used to reduce foaming.

Also included as presently more preferred resins in the present invention are non-isocyanate resins such as water reactive liquid organometallic compounds. These resins are especially preferred as an alternative to isocyanate resin systems. Water-curable resin compositions suitable for use in an orthopedic cast consist of a water-reactive liquid organometallic compound and an organic polymer. The organometallic compound is a compound of the formula $(R^1O)_xMR^2_{(y-x)}$ wherein: each $R^1$ is independently a $C_1$–$C_{100}$ hydrocarbon group, optionally interrupted in the backbone by 1–50 nonperoxide —O—, —S—,

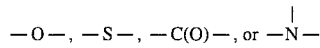

groups; each $R^2$ is independently selected from the group consisting of hydrogen and a $C_1$–$C_{100}$ hydrocarbon group, optionally interrupted in the backbone by 1–50 nonperoxide

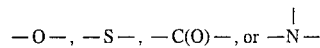

groups; x is an integer between 1 and y, inclusive; y is the valence of M; and M is boron, aluminum, silicon, or titanium. The organic polymer is either an addition polymer or a condensation polymer. Addition polymers are preferably utilized as the organic polymer constituent. Particularly useful addition polymers are those made from ethylenically unsaturated monomers. Commercially available monomers, from which such addition polymers can be formed, include but are not limited to, ethylene, isobutylene, 1-hexene, chlorotrifluoroethylene, vinylidene chloride, butadiene, isoprene, styrene, vinyl napthalene, ethyl acrylate, 2-ethylhexyl acrylate, tetrahydrofurfuryl acrylate, benzyl acrylate, poly(ethylene oxide) monoacrylate, heptafluorobutyl acrylate, acrylic acid, methyl methacrylate, 2-dimethylaminoethyl methacrylate, 3-methacryloxypropyltris(trimethylsiloxy)silane, isobutyl methacrylate, itaconic acid, vinyl acetate, vinyl stearate, N,N-dimethylacrylamide, tert-butyl acrylamide, acrylonitrile, isobutyl vinyl ether, N-vinyl pyrrolidinone, vinyl azlactone, glycidyl methacrylate, 2-isocyanatoethyl methacrylate, maleic anhydride, vinyl triethoxysilane, vinyl tris(2-methoxyethoxy)silane, and 3-(trimethoxysilyl)propyl methacrylate. Polymers bearing hydrolyzable functionality are preferred. An acidic or basic catalyst may be used to accelerate the water cure of these compositions. Strong acid catalysts are preferred.

Also included as presently more preferred resins in the instant invention are alkoxysilane terminated resins, i.e., prepolymers or oligomers, having a number average molecular weight of about 400–10,000, preferably about 500–3,000. A polymer forms upon contacting the alkoxysilane terminated prepolymer with water as a result of condensation of molecules of this prepolymer with other molecules of the same prepolymer. Each molecule of the prepolymer or oligomer contains at least one hydrolyzable terminal alkoxysilane group. Compounds of Formula I useful in the resin compositions of the present invention may contain one to six terminal alkoxysilane groups per molecule. Preferably, the alkoxysilane terminated resin is a urethane-based resin, i.e., a prepolymer containing —NH—C(O)—O—group(s), or a urea resin, i.e., a prepolymer containing

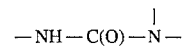

group(s), or a resin containing both urea and urethane groups.

The water-reactive alkoxysilane terminated resin having at least one hydrolyzable terminal alkoxysilane group per molecule is preferably a compound of the formula (Formula I):

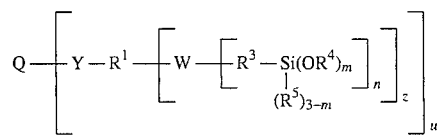

wherein:

Q is a polyol residue;

W is —NH—C(O)—X($R^2_{2-n-q}$)— or —X—C(O)—NH—;

X is $-\overset{|}{N}-$, —O—, or —S—;

Y is $-\overset{|}{N}-$, —O—, —S—, carbamylthio (—S—C(O)—NH—), carbamate (—O—C(O)—NH—), or substituted or N-substituted ureido (—N(C(O)—NH—)—);

$R^1$ is a substituted or unsubstituted divalent bridging $C_1$–$C_{200}$ hydrocarbon group, optionally interrupted in the backbone by 1–50 nonperoxide —O—, —C(O)—, —S—, —SO$_2$—, —NR$^6$—, amide (—C(O)—NH—), ureido (—NH—C(O)—NH—), carbamate (—O—C(O)—NH—), carbamylthio (—S—C(O)—NH—), unsubstituted or N-substituted allophonate (—NH—C(O)—N(C(O)—O—)—), unsubstituted or N-substituted biuret (—NH—C(O)—N(C(O)—NH)—), and N-substituted isocyanurate groups;

$R^2$ can be present or absent, and is selected from the group consisting of H and a substituted or unsubstituted $C_1$–$C_{20}$ hydrocarbon group, optionally interrupted in the backbone by 1–10 nonperoxide —O—, —C(O)—, —S—, —SO$_2$—, or —NR$^6$— groups;

$R^3$ is a substituted or unsubstituted divalent bridging $C_1$–$C_{20}$ hydrocarbon group, optionally interrupted in the backbone by 1–5 nonperoxide —O—, —C(O)—, —S—, —SO$_2$—, or —NR$^6$— groups;

$R^4$ is a $C_1$–$C_6$ hydrocarbon group or —N=C($R^7$)$_2$;

each $R^5$ and $R^7$ is independently a $C_1$–$C_6$ hydrocarbon group;

$R^6$ is a H or a $C_1$–$C_6$ hydrocarbon group;

n=1–2 and q=0–1, with the proviso that when X is N, n+q=1, and when X is S or O, n+q=2;

u=the functionality of the polyol residue=0–6, with the proviso that when u=0, the compound of Formula I is

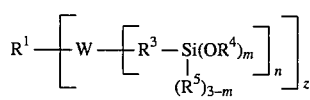

It is to be understood that each "$R^3$—Si($R^5$)$_{3-m}$(OR$^4$)$_m$" moiety can be the same or different. When used in Formula I, the Y and $R^1$ groups that are not symmetric, e.g., amide (—C(O)—NH—) and carbamylthio (—S—C(O)—NH—) groups, are not limited to being bound to adjacent groups in the manner in which these groups are represented herein. That is, for example, if $R^1$ is carbamate (represented as —O—C(O)—NH—), it can be bound to Y and W in either of two manners: —Y—O—C(O)—NH—W— and —W—O—C(O)—NH—Y—.

Herein, when it is said that "each" $R^5$ and $R^7$ is "independently" some substituent group, it is meant that generally there is no requirement that all $R^5$ groups be the same, nor is there a requirement that all $R^7$ groups be the same. As used herein, "substituted" means that one or more hydrogen atoms are replaced by a functional group that is nonreactive, e.g., to hydrolysis and/or condensation and noninterfering with the formation of the cured polymer.

In preferred materials $R^1$ is selected from the group consisting of a substituted or unsubstituted $C_1$–$C_{200}$ alkyl, a substituted or unsubstituted $C_1$–$C_{200}$ acyl, and groups of up to 50 multiples of a $C_3$–$C_{18}$ cycloalkyl, a $C_7$–$C_{20}$ aralkyl, and a $C_6$–$C_{18}$ aryl. By this, it is meant that $R^1$ can be a long chain containing, for example, up to 50 repeating $C_6$–$C_{18}$ aryl groups. More preferably, $R^1$ is selected from the group consisting of a substituted or unsubstituted $C_1$–$C_{100}$ alkyl, a substituted or unsubstituted $C_1$–$C_{100}$ acyl, and groups of up to 30 multiples of a $C_5$–$C_8$ cycloalkyl, and a $C_6$–$C_{10}$ aryl. Most preferably, $R^1$ is selected from the group consisting of a $C_1$–$C_{20}$ alkyl, a $C_1$–$C_8$ acyl, and groups of up to 5 multiples of a $C_5$–$C_8$ cycloalkyl, and a $C_6$–$C_{10}$ aryl. In each of the preferred $R^1$ groups, the backbone is optionally interrupted by 1–20 nonperoxide —O—, —C(O)—, —S—, —SO$_2$—, —NR$^6$—, amide, ureido, carbamate, carbamylthio, allophonate, biuret, and isocyanurate groups.

In each of the more preferred $R^1$ groups, the backbone is optionally interrupted by 1–10 nonperoxide —O—, —C(O)—, —S—, —SO$_2$—, —NR$^6$—, amide, ureido, carbamate, carbamylthio, allophonate, biuret, and isocyanurate groups. In each of the most preferred $R^1$ groups, the backbone of each of the $R^1$ groups is not interrupted by any of these groups.

In preferred materials, each of $R^2$ and $R^3$ is independently selected from the group consisting of a substituted or unsubstituted $C_1$–$C_{20}$ alkyl, a substituted or unsubstituted $C_2$–$C_8$ alkenyl, and groups of up to 10 multiples of a $C_3$–$C_{18}$ cycloalkyl and a $C_6$–$C_{18}$ aryl. More preferably, each $R^2$ and $R^3$ is independently selected from the group consisting of a substituted or unsubstituted $C_1$–$C_{10}$ alkyl, a substituted or unsubstituted $C_2$–$C_{10}$ alkenyl, a $C_5$–$C_8$ cycloalkyl, and a $C_6$–$C_{10}$ aryl. Most preferably, each $R^2$ and $R^3$ is independently selected from the group consisting of a $C_1$–$C_6$ alkyl, a $C_2$ alkenyl, a $C_5$–$C_8$ cycloalkyl, and a $C_6$ aryl. In each of the preferred $R^2$ and $R^3$ groups, the backbone is optionally interrupted by 1–5 nonperoxide —O—, —C(O)—, —S—, —SO$_2$—, and —NR$^6$— groups. In optimal resins, the backbone of each of the $R^2$ and $R^3$ groups is not interrupted by any of these groups.

In preferred materials, each of $R^4$, $R^5$, $R^6$, and $R^7$ is independently a $C_1$–$C_6$ alkyl group. More preferably, each is a $C_1$–$C_3$ alkyl group. A single prepolymer according to Formula I can be used in the resin composition of the present invention. Alternatively, a mixture of several different prepolymers according to Formula I can be used in the resin composition.

Optionally, the scrims of the present invention are coated with a resin which incorporates microfiber fillers. These preferred orthopedic bandages enjoy many benefits, for example, resins which incorporate microfiber fillers exhibit: a dramatic increase in strength when coated on the backings of the present invention; an increased "early strength" upon curing; an improved durability and increased modulus; better layer-to-layer lamination strength; a lower exotherm upon setting; and a lower effective resin cost compared to resins which do not incorporate such microfiber fillers. In addition, resin suspensions employing the microfiber fillers of the present invention exhibit generally very little increase in resin viscosity-thereby ensuring easy unwind of the casting bandage and good handling properties such as drapability. Suitable microfibers for use in the present invention include those microfiber fillers disclosed in U.S. patent application Ser. No. 08/008,755 which is herein incorporated by reference.

In addition to the application of the present invention to the field of orthopedic casting tapes, other uses may include wrapping and/or joining pipes, cables or the like; patching or bridging gaps to provide a surface for filling and repairs; etc.

The following examples are offered to aid in understanding of the present invention and are not to be construed as limiting the scope thereof. Unless otherwise indicated, all parts and percentages are by weight.

EXAMPLES

Ring strength was measured as described in the following procedure. A cylindrical ring comprising 6 layers of the resin-coated material was formed by taking a roll of the resin-coated material from its storage pouch and immersing the roll completely in deionized water having a temperature of about 27° C. for about 30 seconds. The width of the ring formed was the same as the width of the resin-coated material employed, namely, 7.62 cm. The roll of resin-coated material was then removed from the water and the material was wrapped around a 5.08 cm diameter mandrel covered with a thin stockinet (such as 3M Synthetic Stockinet MS02) to form 6 complete uniform layers using a controlled wrapping tension of about 45 grams per centimeter width of material. Each cylinder was completely wound within 30 seconds after its removal from the water.

After 7 to 20 minutes from the initial immersion in water, the cured cylinder was removed from the mandrel. Ring strength was determined 24 hours after initial immersion in water, i.e., those samples were allowed to cure for 24 hours in a controlled atmosphere of 25° C.±2° C. and 55%±5% relative humidity prior to testing.

At the appropriate time each cylinder was then placed in a fixture in a commercial testing machine, e.g., an Instron 1122 instrument, and compression loads were applied to the cylindrical ring sample along its exterior and parallel to its axis. The cylindrical ting was placed lengthwise between the two bottom bars of the fixture (the bars being 1.9 cm wide, 1.3 cm in height, and 15.2 cm long), with the bars spaced about 4 cm apart. The inside edges of the bars were machined to form a curved surface having a 0.31 cm radius. A third bar (0.63 cm wide, 2.5 cm high, and 15.2 cm long) was then centered over the top of the cylinder, also parallel to its axis. The bottom or contacting edge of the third bar was machined to form a curved surface having a 0.31 cm radius. The third bar was brought down to bear against and crush the cylinder at a speed of about 5 cm/min. The maximum force which was applied while crushing the cylinder was then recorded and divided by the width to yield the "ring strength," which in this particular instance is the "dry strength" (expressed in terms of force per unit length of the cylinder, i.e., newtons/cm). For each material, at least 5 samples were tested, and the average peak force applied was then calculated and reported as the dry "ring strength."

To measure the "wet ting strength", the same procedure was followed as for the "dry ring strength", except that after curing for 24 hours, the cylinder was then immersed in water at about 45° C. for about 30 minutes, and then allowed to dry at room temperature and pressure for about 15 minutes. The cylinder was then placed in the instrument and crushed as described hereinabove in order to determine the "wet ring strength" thereof.

To measure the "warm wet ring strength" of the cylinder, the procedure was followed exactly as set forth for the "wet ting strength" measurement above, with the exception that the cylinder was placed in the fixture and crushed immediately after removal from the 45° C. water bath and was not allowed to dry at all.

Ring delamination was measured as described in the following procedure. A cylindrical ring comprising 6 layers of the resin-coated material was formed by taking a roll of the resin-coated material from its storage pouch and immersing the roll completely in deionized water having a temperature of about 27° C. for about 30 seconds. The width of the ting formed was the same as the width of the resin-coated material employed, namely, 7.62 cm. The roll of resin-coated material was then removed from the water and the material was wrapped around a 5.08 cm diameter mandrel covered with a thin stockinet (such as 3M Synthetic Stockinet MS02) to form 6 complete uniform layers using a controlled wrapping tension of about 45 grams per centimeter width of material. A free tail of about 15.24 cm was kept and the balance of the roll was cut off. Each cylinder was completely wound within 30 seconds after its removal from the water.

After 15 to 20 minutes from the initial immersion in water, the cured cylinder was removed from the mandrel, and after 30 minutes from the initial immersion in water its delamination strength was determined.

A determination of delamination strength was done by placing the free tail of the cylindrical sample in the jaws of the testing machine, namely, an Instron Model 1122 machine, and by placing a spindle through the hollow core of the cylinder so that the cylinder was allowed to rotate freely about the axis of the spindle. The Instron machine was then activated to pull on the free tail of the sample as a speed of about 127 cm/min. The average force required to delaminate the wrapped layers over the first 33 centimeters of the cylinder was then recorded in terms of force per unit width of sample (newtons/cm width). For each material, at least 5 samples were tested, and the average delamination force was then calculated and reported as the "delamination strength."

Example 1

Shrink Yarns for Use in Compaction of a Fiberglass Knit Casting Tape

Most synthetic polymeric fibers exhibit some degree of shrinkage when heated. In order to be useful in the present invention the heat shrink fibers should generate a sufficient force and a sufficient displacement during their shrinkage to adequately compact the knit tape. Suitable heat shrink fibers are preferably capable of performing this compaction when present in an amount that can be successfully desized without causing excessive degradation of the fiberglass (e.g., present at a relatively low denier).

The percent shrinkage and shrinkage force for the following commercially available yarns was measured as a function of temperature.

TABLE 1a

| Yarn | Denier | Composition |
| --- | --- | --- |
| Dupont[1] 440-100-R02-52 | 440 | Multifilament Polyester |
| Dupont 220-50 | 220 | Multifilament Polyester |
| Celanese[2] 90/36, T770 brt, ¼ turn | 90 | Multifilament Polyester |
| Celanese 100/33 | 100 | Multifilament Polyester |
| Shakespeare[3] MX-306 0.009 401 1010 10A (LDPE) | 340 | Monofilament polyethylene |
| Shakespeare 283 | 283 | Monofilament Polyester |

[1]Dupont, Fibers Div. Wilmington DE
[2]Celanese Fibers, Celanese Chemical Co., New York, NY
[3]Shakespeare Monofilament Div., Columbia, S.C.

The data presented in Tables 1b and 1c was generated using a Testrite™ MK IV Shrinkage-Force Tester (available from Testrite Ltd., West Yorkshire, England). Percent shrinkage was measured using the following test method. The Testrite™ apparatus was preheated to the desired temperature range and a sample of yarn about 600 mm long was clamped at one end to the fixed jaw clamp and allowed to drape over the take up drum. A clip weight (1.78 gm) was attached to the other end of the yarn and allowed to hang about 100 mm below the center of the drum. This weight is used primarily to take out the catenary from the sample. With the sample in position on the drum, the drum was rotated so the digital readout displays 0 (zero). The carriage assembly was then carefully pushed forward slowly into position in the heat zone. The heat will cause the sample to shrink and thus rotate the take up drum. Maximum shrinkage of the sample at any given operating temperature is deemed to have taken place when the digital readout holds steady.

Shrinkage force was similarly measured according to the following test. The Testrite™ apparatus was fitted with the load cell and jaw attachment apparatus secured to the carriageway. The sample was secured to the fixed jaw clamp and draped over the take up drum as previously described.

After removing the catenary from the sample (e.g., by hanging a 1.78 gm weight from the free end of the sample) the load cell clamp was secured to the sample. The carriage assembly was then carefully pushed forward slowly into position in the preheated heat zone. The heat will cause the sample to shrink and thus apply tension to the load cell. Maximum shrinkage force of the sample at any given operating temperature is then recorded.

TABLE 1b

Percent Shrinkage for Various Yarns

| Temp (°C.) | DuPont 440 | Celanese 90 | Celanese 100 | Shakespeare MX-306 |
|---|---|---|---|---|
| 50 | — | — | — | 3 |
| 60 | — | — | — | 7 |
| 70 | — | — | — | 14 |
| 80 | — | — | — | 16 |
| 90 | — | — | — | 18 |
| 100 | — | — | — | 21 |
| 110 | — | — | — | — |
| 120 | — | — | — | — |
| 130 | 6 | 5 | — | — |
| 140 | 8 | 6 | — | — |
| 150 | 10 | 7 | — | — |
| 160 | 11 | 8 | 11 | — |
| 170 | 13 | 9 | 12 | — |
| 180 | 14.5 | 10.5 | 11 | — |
| 190 | 16 | 12 | 14 | — |
| 200 | 19 | 14 | 14 | — |
| 210 | 21 | 10 | 15 | — |
| 220 | 24.5 | 20 | 16 | — |
| 230 | 27 | 24 | 20 | — |
| 240 | — | 29 | 24 | — |
| 250 | — | — | 28 | — |

Table 1b depicts the percentage of shrinkage for various organic yarns which have been subjected to a heat cycle. As can be readily observed (and within the temperature ranges shown) the yarns generally exhibit more shrinkage as they are heated to higher temperatures. Notably, the "Shakespeare MX-306" yarn (comprising a polyethylene polymer) exhibits its shrinkage at a lower temperature than the other yarns (which each comprise a polyester polymer).

TABLE 1c

Shrinkage Force For Various Yarns (N)

| Temp (°C.) | Celanese[1] 90 | Celanese[2] 90 | Celanese[3] 90 | DuPont 220 | DuPont 440 | Shakespeare PX-301 |
|---|---|---|---|---|---|---|
| 140 | 0.3 | 0.7 | 1 | 0.7 | | 0.7 |
| 150 | 0.3 | 0.6 | 1.1 | 0.7 | | 1.0 |
| 160 | 0.3 | 0.7 | 1.1 | 0.8 | | 1.0 |
| 170 | 0.2 | 0.8 | 1.1 | 0.8 | | 1.1 |
| 180 | 0.4 | 0.7 | 1.2 | 0.7 | 1.5 | 1.1 |
| 190 | 0.3 | 0.6 | 1.2 | 0.6 | 1.4 | 1.1 |
| 200 | 0.1 | 0.8 | 1.2 | 0.6 | 1.3 | 1.0 |
| 210 | 0.1 | 0.8 | 0.9 | 0.5 | 1.3 | 0.9 |
| 220 | 0.3 | 0.5 | 1.1 | 0.6 | 1.3 | 0.8 |
| 230 | 0.3 | 0.7 | 1.1 | | 1.2 | 0.7 |

[1]One yarn.
[2]Two yarns.
[3]Three yarns.

Table 1c depicts the shrinkage force (Newtons) for various organic yarns. These yarns were preloaded with a weight of approximately 1.73 g prior to testing. The data for the Celanese 90 denier 36 filament yarn shown in Table 1c indicates that the shrink force is generally proportional to the number of yarns used.

Example 2

Compaction of a Fiberglass Knit Casting Tape

Several of the yarns from Example 1 were inserted into a fiberglass knit structure and used to compact the knit structure. The yarns were placed in as a single needle lay-in in a fiberglass fabric with the following parameters: Mayer Raschel 60 inch knitter (available from Meyer Textile Machinery Corp., Greensboro, N.C. as HDR10EHW ); 18 gauge (7.09 needles/cm); front runner length (chain stitch) 403.9 cm; back runner length (lay-in stitch) 355.6 cm; and middle runner length (shrink yarn laying stitch) 91.4 cm.

Owens Corning fiberglass (available from Owens Corning, Aiken, S.C. as ECG 75 1/0 0.7Z 620) was used for both the front and back bar.

Heat shrink yarns were inserted into the knit using a third bar (i.e., the middle bar as previously described). As described below, the heat shrink yarns were not placed in every wale but were spaced into about every third or every sixth wale. The fabrics had the following physical properties: 10.4 cm width; 5.39 courses per cm; and 29.6 gm per meter length.

The fabric was heat shrunk using forced hot air and then wound up. "Percent compaction" was measured by first marking off a known length of fabric and measuring the length after heat treatment. Note that the marked off section was positioned in the middle of a longer piece of fabric in order to ensure that the heat shrink yarn would not slip during compaction. The percent compaction was calculated as:

$$\frac{\text{initial length} - \text{shrunk length}}{\text{initial length}} \times 100 = \text{percent compaction}$$

The following table summarizes the results:

TABLE 2a

| Yarn | Peak shrink force[1], (N) | Denier | In-laid every: | Percent compaction (%) |
|---|---|---|---|---|
| Dupont 440 Celanese 90 | 1.5 | 440 | 6 wales | 15–18% |
| 1 end | 0.4 | 90 | | |
| 2 ends | 0.8 | 180 | | |
| 3 ends | 1.2 | 270 | 6 wales | 10–12% |
| | | | 3 wales | <10% |
| Shakespeare PX-301 | 1.1 | 283 | 6 wales | >15% |
| | | | 3 wales | >15% |
| Shakespeare MX-306 | 1.5 | 340 | 6 wales | 17–20% |

[1]Tested as described in Example 1.

The above data indicates that in order to compact the fabric of this specific construction a force greater than about 1N is desirable. Furthermore, the data suggests that a monofilament of equivalent denier appears to yield greater compaction than a multifilament yarn.

Example 3

Effect of Winding Tension

A 7.62 cm knitted fiberglass fabric containing Dupont 440-100-R02-52 multifilament polyester shrink yarn was produced with the following parameters: Owens Corning fiberglass ECG 75 1/0 620; heat shrink yarn: Dupont 440-100-R02-52 polyester; Mayer Raschel 229 cm 18 gauge (7.1 needles/cm) knitter; knit pattern: 0/2, 2/0 (front bar); 0/0, 2/2 (middle bar); and 6/6, 0/0 (back bar); thread up: front and back- full, middle bar: single needle in-lay spaced every 6th wale; front runner length (fiberglass chain stitch ) 406 cm; back runner length (fiberglass lay-in stitch ) 274 cm; middle bar runner length (polyester heat shrink lay-in stitch ) 86.4 cm. Owens Corning fiberglass (available from Owens Corning, Aiken, S.C. as ECG 75 1/0 620) was used for both the front and back bar. Note that the heat shrink yarn was in-laid 180 degrees out of phase with the fiberglass inlay and across a single needle in an alternating pattern of: 1 wale in and the next five wales out. The exact middle bar threading was (1,5,1,5,1,5,1,5,1,4,1,5,1,5,1,5,1,5,1) where 1 indicates a wale containing a heat shrink yarn, 4 indicates 4 wales without the heat shrink yarn, and 5 indicates 5 wales without the heat shrink yarn.

In order to determine the effect of wind-up tension on the temperature reached during desizing within a rolled up "jumbo" of fabric the following experiment was conducted.

A sample of approximately 27.4 meters of the knit structure was wound by hand into either a "tight" or a "loose" roll. The tight roll was produced by winding the knit as tightly as could be performed by hand without plastically deforming the heat shrunk yarn. The loose roll was produced by applying very little tension to the knit during windup. The tightly wound roll had a circumference of approximately 36.5 cm and the loosely wound roll had a circumference of approximately 44.0 cm. During the winding operation two small plastic tubes were inserted between the layers (as guides for inserting thermocouple sensors), the first approximately at the middle of the roll diameter (i.e., near the core) and the second at approximately 1.3 cm from the outer edge. The plastic guides were removed prior to desizing. The rolls were placed in a forced air recirculating oven in separate cycles. The oven was brought up to 500° C. and held for 8 to 10 hours at that temperature. The temperature of the roll was recorded as a function of time. Peak temperatures are shown below:

TABLE 3a

| Roll Tension | Position: Mid roll | | Outer 1 cm | |
|---|---|---|---|---|
| | Peak temp. (°C.) | Time (min.) | Peak temp. (°C.) | Time (min.) |
| Tight | 571 | 76 | 544 | 60 |
| Loose | 720 | 62 | 549 | 32 |

The data indicates that both rolls heated up significantly higher than the oven temperature. The data also indicates that the loosely wound roll became significantly hotter in the center of the roll than the tightly wound roll. This higher temperature could lead to degradation of the fabric integrity. The loosely wound roll also reached its peak exotherm temperature more quickly than the tightly wound roll. Although not intending to be bound by theory, these results are believed to be in part due to the different amounts of oxygen available within the roll. The oxygen being necessary for the combustion of the heat shrink yarn and affecting the combustion rate.

Notably, an important advantage of using heat shrink yarns to impart compaction to a knit fabric is the ability to wind the knit fabric under tension while not thereby removing the extensibility.

Example 4

Coated Fabric

A 10.2 cm knit produced with the knitting parameters shown in Ex. 3 was heat shrunk in a tunnel oven at a temperature of 218° C. The fabric was observed to shrink approximately 15% during this heat treatment process. The shrunken fabric was then wound into a fairly loose roll under low tension. In order to avoid sagging in the oven which would reduce the compactness of the fabric the roll was supported by wrapping fiberglass fabric through the aluminum core and around the exterior of the roll. This wrap served to support the weight of the fabric and prevent undesirable sagging.

The tape was heat set and cleaned in a recirculating hot air oven at 427° C. for 8 hours. The heat set fabric was coated using a very low tension coater with the following isocyanate functional prepolymer resin:

TABLE 4a

| Chemical | Manufacturer | Eq wt. | Wt. % |
|---|---|---|---|
| Isonate 2143L | Dow Chemical | 144.7 | 57.7 |
| pToluenesulfonyl chloride | Akzo | | 0.05 |
| Antifoam DB-100 | Dow Corning | | 0.18 |
| Butylated hydroxytoluene | Shell Chemical | | 0.48 |
| Pluronic F-108 | BASF | | 4.00 |
| MEMPE | 3M | | 1.15 |
| PPG-2025 | Union Carbide[1] | 1019.25 | 21.22 |
| LG-650 | Union Carbide[1] | 85.49 | 5.67 |
| Niax E-562 | Union Carbide[1] | 1753.13 | 9.55 |

[1]Formerly available from Union Carbide now available from Arco Chemical Co., So. Charlestown, WV The resin was coated on the 10.2 cm wide fabric produced as described above at a coating weight of 40% by weight. The product was rolled up on a 1.27 cm diameter polyethylene core into individual rolls approximately 320 cm long and the rolls were sealed in conventional moisture proof aluminum foil laminate pouches. The product was tested for the properties listed below according to the test methods described above. All values are the mean of 5 samples unless otherwise noted.

TABLE 4b

| Test | Result |
|---|---|
| Ring delamination[1] | 8.9 N/cm width |
| Dry Strength | 79.5 N/cm |
| Wet Strength | 42.0 N/cm |
| Warm Wet Strength | 25.6 N/cm |

[1]Three samples tore before a delamination value could be recorded. The result shown is an average of the two samples that did not tear.

Example 5

Desize Cycle Optimization

In order to prevent degradation of the fabric it is important to keep the temperature in the jumbo as low as possible while still removing the yarn and combustion products completely. This experiment investigated various temperature profiles in the oven cycle and the effect on internal fabric temperatures.

A 7.62 cm knitted fiberglass fabric containing Dupont 440-100-R02-52 multifilament polyester shrink yarn was produced with the following parameters: Owens Corning fiberglass ECG 75 1/0 620; heat shrink yarn: Dupont 440/100/R02/52 polyester; Mayer Raschel 229 cm knitter; 18 gauge (7.1 needles/cm); knit pattern: 0/2, 2/0 (front bar); 0/0, 2/2 (middle bar); and 8/8, 0/0; (back bar); thread up: front and back-full, middle bar: single needle in-lay spaced every 6th wale; front runner length (fiberglass chain stitch ) 406 cm; back runner length (fiberglass lay-in stitch) 368 cm; middle bar runner length (polyester heat shrink lay-in stitch) 96.5 cm. Owens Corning fiberglass (available from Owens Corning, Aiken, S.C. as ECG 75 1/0 620) was used for both the front and back bar. Note that the heat shrink yarn was in-laid 180 degrees out of phase with the fiberglass in-lay and across a single needle in an alternating pattern of: 1 wale in and the next five wales out. The exact middle bar threading was (1,5,1,5,1,5,1,5,1,4,1,5,1,5,1,5,1,5,1) where 1 indicates a wale containing a heat shrink yarn, 4 indicates 4 wales without the heat shrink yarn, and 5 indicates 5 wales without the heat shrink yarn.

The tape produced had a nominal 10.2 cm width and was wound up using a surface winder to a roll diameter of approximately 45.7 cm. The fabrics had the following physical properties: 10.4 cm width; 5.79 courses per cm; and a weight of 16.6 gm per 240 courses.

The rolls were heat shrunk by passing the material as a single layer through a tunnel oven (approximately 1 meter in length) set at a temperature of 249° C. at a speed of 96.5 cm/min. and supported on a metal belt conveyor. After heat shrinking the tape was wound back up into roll form on a 7.62 cm diameter aluminum roll. Individual rolls were heat set and cleaned in a small recirculated oven. The temperature cycles were varied and the temperature monitored using a set of thermocouples. Thermocouples were placed between layers of fabric at radial positions approximately 10, 50, and 90% of the roll length away from the core of the roll. The peak temperatures reached at each of these points for each cycle are presented below:

TABLE 5a

| | Oven operating conditions | | Peak temperature of roll at position indicated | | |
|---|---|---|---|---|---|
| Run # | temperature (°C.) | cycle time (hours) | 10% | 50% | 90% |
| 1 | 399 | 8 | 532 | 538 | 460 |
| 2 | 427 | 8 | 552 | 554 | 521 |
| 3 | 399 | 8 | 552 | 552 | 518 |
| 4 | 343° C. for 4 hours, then 427° C. for 4 hrs | | 510 | 532 | 488 |
| 5 | 371° C. for 4 hours, then 427° C. for 4 hrs | | 468 | 496 | 438 |

After treatment in the oven all the materials were observed to be clean. Run 5 is presently preferred.

Example 6

Effect of Heat Shrink Yarn on Web Integrity

Samples of heat set cleaned fabric similar to that described in Ex. 4 were studied to determine whether there is any localized degradation of the fiberglass due to the added combustible heat shrink yarn (DuPont 440 yarn). The fabric samples were sized by immersing the fabric in a 1% aqueous solution of Triple Concentrate Downy™ fabric softener (available from Proctor and Gamble Co., Cincinnati, Ohio). Samples were taken from the midpoint of the roll which had been exposed to the operating conditions of Run #5 of Table 5a. Wales at selected positions across the width of the tape were removed and tested for tensile strength using an Instron model 1122 testing machine (Instron Corp., Park Ridge, Ill). The average value of three samples is shown below in Table 6a.

TABLE 6a

| Wale number | Tensile strength (N) |
|---|---|
| 1[1] | 4.89 |
| 2 | 6.14 |
| 3 | 7.47 |
| 4 | 6.67 |
| 5 | 6.23 |
| 6 | 7.47 |

TABLE 6a-continued

| Wale number | Tensile strength (N) |
|---|---|
| 7[1] | 6.14 |
| 8 | 5.60 |
| 9 | 6.32 |
| 10 | 7.92 |
| 11 | 9.12 |
| 12 | 6.72 |
| 13[1] | 4.45 |
| 14 | 6.14 |
| 15 | 8.10 |
| 16 | 9.12 |
| 17 | 7.03 |
| 18 | 5.43 |
| 19[1] | — |

[1]A heat shrink yarn was inserted at these wale positions.

The results clearly show that near the local vicinity of a heat shrink yarn the fiberglass yarns are degraded. While not intending to be bound by theory, this result is believed to be due to the fiberglass yarn having been exposed to a higher localized temperature caused by the combustion of the heat shrink yarn.

Similar knits to the above knit were produced except that the heat shrink yarn was replaced with three yarns in each position of the Celanese denier polyester shrink yarn (C90) or with a single yarn of the Shakespear PX-301 283 denier polyester monofilament (PX-301). Note that the PX-301 knit was only 7.62 cm wide and was not heat shrunk prior to heat setting. The individual wale tensile strengths for these fabrics is shown below in Table 6b:

TABLE 6b

| | Tensile strength (N) | |
|---|---|---|
| Wale number | Celanese C90 | Shakespear PX301 |
| 6[1] | 8.1 | 9.4 |
| 7 | 9.9 | 9.1 |
| 8 | 10.9 | 9.3 |
| 9 | 11.4 | 13.7 |
| 10 | 12.1 | 8.5 |
| 11 | 12.1 | 9.5 |
| 12[1] | 9.0 | 9.2 |
| 13 | 9.3 | 8.5 |
| 14 | 8.9 | 11.4 |

TABLE 6b-continued

| | Tensile strength (N) | |
|---|---|---|
| Wale number | Celanese C90 | Shakespear PX301 |
| 15 | 8.1 | 9.0 |
| 16 | 12.2 | 11.7 |
| 17 | 9.0 | 9.0 |
| 18[1] | 8.4 | 8.8 |

[1]A heat shrink yarn was inserted at these wale positions.

Note that the C90 sample shows loss of integrity near the local area around the heat shrink yarn. The PX-301 sample, however, does not show this effect as clearly. Note that all of the wale strength values are significantly higher than for the knit containing the Dupont 440 denier polyester.

A similar experiment was conducted using Shakespear MX-306 polyethylene monofilament and no heat shrink yarn (control). For all materials a sample of fabric was also stretched in tensile in the Instron 1122 and the load at which wale breakage occurred was recorded. A summary of the data is given in the table below (values recorded in Newtons). All values are mean values of at least three trials.

TABLE 6c

| Test | Control | Dupont 440 (440d) | Celanese C90 (270d) | Shakespear PX301 (283d) | Shakespear MX306 (340d) |
|---|---|---|---|---|---|
| Fabric Stretch Test load at wale break | 53–76 | 18–22 | 31–53 | 18–27 | 44–53[1] |
| Indiv. wale tensile (wale w/ shrink yarn) | 12.5 | 4.4 | 8.0 | 8.9 | 6.7 |
| Indiv. wale tensile (wales w/o shrink yarn) | 12.5 | 8.9 | 12.2 | 13.3 | 6.7 |

[1]Individual wales did not break before the fabric ripped at the clamp site.

The data clearly shows that the fabrics containing the lower denier polyester materials (C90 or PX-301) retain much more integrity than the fabric containing the higher denier polyester heat shrink yarn (Dupont 440).

Example 7

Fabric compacted with a multifilament POY yarn

A 7.62 cm knitted fiberglass fabric containing Celanese partially oriented yarn (hereinafter "POY") was produced with the following parameters: Owens Corning fiberglass ECG 75 1/0 620; heat shrink yarn: Celanese POY Style 661,227 denier; Mayer Raschel 229 cm knitter; 18 gauge (7.0866 needles/cm); knit pattern: 2/0,0/2 (front bar); 0/0,2/2 (middle bar); and 0/0,8/8 (back bar); thread up: front and back-full; middle bar: single needle in-lay spaced every third wale; front runner length (fiberglass chain stitch ) 419 cm; back runner length (fiberglass lay-in stitch ) 338 cm; take-up length per rack: 94 cm.

Owens Corning fiberglass (available from Owens Corning, Aiken, S.C. as ECG 75 1/0 620) was used for both the front and back bar. Note that the heat shrink yarn was in-laid in phase with the fiberglass in-lay and across a single needle in an alternating pattern of: 1 wale in and the next two wales out. The exact middle bar threading was (0101001001001001001001001001001001001001001010 01001001010) where 1 indicates a wale containing a heat shrink yarn and 0 indicates wales without the heat shrink yarn.

A nominal 10.2 cm fabric was produced and wound up by hand. The fabric was heat shrunk by heating with saturated 10.3N/cm² steam. The fabric contracted about 12–15%. Once desized the knit would have between about 40 and 45% extensibility.

Various modifications and alterations of this invention will be apparent to those skilled in the art without departing from the scope and spirit of this invention, and it should be understood that this invention is not limited to the illustrative embodiments set forth herein.

What is claimed is:

1. A method of making an orthopedic casting bandage, comprising the steps of:
   knitting a high modulus yarn having a modulus of elasticity greater than 8×10⁶ lbs/square inch, and a heat shrinkable yarn to form a fabric;
   heating said knit fabric to a sufficient temperature to cause said heat shrinkable yarn to shrink, thereby compacting said fabric; and then
   coating said knit fabric with a curable or hardenable liquid resin.

2. A method according to claim 1, further comprising the step of:
   heat setting said compacted fabric prior to coating said fabric with said resin thereby combusting said heat shrinkable yarn, and wherein said high modulus yarn comprises fiberglass.

3. A method according to claim 1, wherein said casting bandage has from about 25% to about 75% extensibility in the elongated direction when a 2.63N tensile load or force is applied per 1 cm wide section of the fabric.

4. A method according to claim 2, wherein said curable resin is selected from the group consisting of water-curable resins comprising isocyanate-functional prepolymers; water-curable resins comprising a water-reactive liquid organometallic compound and an organic polymer; and alkoxysilane terminated polyurethane prepolymer resins.

5. A method according to claim 2, wherein said resin has a viscosity between about 10 Pa s and 100 Pa s, and wherein said fabric is compacted to between about 20 and 50 percent of its original dimension.

6. A method according to claim 1, wherein said heat shrinkable yarn is knit into said fabric as a lay-in.

7. A method according to claim 1, wherein said heat shrinkable yarn is selected from the group consisting of polyester, polyamide and polyethylene.

8. A method according to claim 1, wherein said heat shrinkable yarn shrinks at a temperature between 70° C. and 300° C.

9. A method according to claim 1, wherein said curable resin is selected from the group consisting of water-curable resins comprising a water-reactive liquid organometallic compound and an organic polymer, alkoxysilane terminated polyurethane prepolymer resins, and isocyanate-functional resins.

10. A method according to claim 1, wherein said curable resin is a water-curable isocyanate-functional resins.

11. A method according to claim 9, wherein said fabric has between about 6 and 70 openings per square cm when under a tensile load of 2.63N/cm width.

12. A method according to claim 1, wherein said fabric was compacted to between about 30 and 90 percent of its original knit dimension.

13. A method according to claim 1, wherein said fabric was compacted to between about 50 and 80 percent of its original knit dimension.

14. A method according to claim 10, wherein said resin has a viscosity between about 10 Pa s and 100 Pa s.

15. A method according to claim 7, wherein said heat shrinkable yarn has a denier between 100 and 500.

16. A method according to claim 8, wherein said heat shrinkable yarn has a denier between 200 and 300.

17. A method of making an orthopedic casting bandage, comprising the steps of:
   knitting a high modulus yarn having a modulus of elasticity greater than 8×10⁶ lbs/square inch, and a heat shrinkable yarn to form a fabric;
   heating said knit fabric to a sufficient temperature to cause said heat shrinkable yarn to shrink, thereby compacting said fabric; and then
   coating said knit fabric, comprising said high modulus yarn and said heat shrink yarn, with a water-curable isocyanate-functional resin.

18. A method according to claim 17, wherein said heat shrinkable yarn is knit into said fabric as a lay-in and is selected from the group consisting of polyester, polyamide and polyethylene, and wherein said casting bandage has from about 25% to about 75% extensibility in the elongated direction when a 2.63N tensile load or force is applied per 1 cm wide section of the fabric.

19. A method according to claim 18, wherein said fabric was compacted to between about 50 and 80 percent of its original knit dimension.

* * * * *

UNITED STATES PATENT AND TRADEMARK OFFICE
CERTIFICATE OF CORRECTION

PATENT NO.: 5,455,060

DATED: October 3, 1995

INVENTOR(S): Scott A. Neamy, James C. Novack and Matthew T. Scholz

It is certified that error appears in the above-identified patent and that said Letters Patent is hereby corrected as shown below:

Col. 1, line 65, "yams" should read -- yarns --.

Col. 2, line 16, "yams" should read -- yarns --.

Col. 2, line 32, "yam" should read -- yarn --.

Col. 2, line 35, "yam" should read -- yarn --.

Col. 2, line 54, "Pads" should read -- Paris --.

Col. 2, line 56, "Pads" should read -- Paris --.

Col. 6, line 29, "Vedagsanstadt" should read -- Verlagsanstadt --.

Col. 6, line 37, ""laying"" should read -- "lay-in" --.

Col. 8, line 13, "wale" should read -- chain stitch --.

Col. 13, line 44, "Coming" should read -- Corning --.

Col. 13, line 60, delete "-O-, -S-,".

Col. 15, line 45, after the equation, add -- m = 2-3; and z = 1-3 --.

Col. 17, line 32, "ting" should read -- ring --.

UNITED STATES PATENT AND TRADEMARK OFFICE
CERTIFICATE OF CORRECTION

PATENT NO.: 5,455,060

DATED: October 3, 1995

INVENTOR(S): Scott A. Neamy, James C. Novack and Matthew T. Scholz

It is certified that error appears in the above-identified patent and that said Letters Patent is hereby corrected as shown below:

Col. 17, line 50, "ting" should read -- ring --.

Col. 17, line 60, "ting" should read -- ring --.

Col. 18, line 4, "ting" should read -- ring --.

Signed and Sealed this

Twenty-fifth Day of March, 1997

Attest:

BRUCE LEHMAN

Attesting Officer

Commissioner of Patents and Trademarks